United States Patent
Koerth et al.

(10) Patent No.: US 9,861,326 B2
(45) Date of Patent: Jan. 9, 2018

(54) MEDICAL EXAMINATION FACILITY

(71) Applicants: Michael Koerth, Fürth (DE); Wolfgang Neuber, Pressath (DE); Peter Rauh, Schnabelwaid (DE)

(72) Inventors: Michael Koerth, Fürth (DE); Wolfgang Neuber, Pressath (DE); Peter Rauh, Schnabelwaid (DE)

(73) Assignee: Siemens Aktiengesellschaft, München (DE)

(*) Notice: Subject to any disclaimer, the term of this patent is extended or adjusted under 35 U.S.C. 154(b) by 139 days.

(21) Appl. No.: 14/666,706

(22) Filed: Mar. 24, 2015

(65) Prior Publication Data
US 2015/0272518 A1 Oct. 1, 2015

(30) Foreign Application Priority Data

Mar. 25, 2014 (DE) .......... 10 2014 205 537
Jun. 12, 2014 (DE) .......... 10 2014 211 269

(51) Int. Cl.
*A61B 6/04* (2006.01)
*A61B 5/055* (2006.01)

(52) U.S. Cl.
CPC .......... *A61B 6/0407* (2013.01); *A61B 5/0555* (2013.01); *A61B 6/0457* (2013.01)

(58) Field of Classification Search
CPC ... A61B 5/0555; A61B 6/0407–6/0492; A61B 5/055; A61G 13/08; B62D 25/10; E05B 15/0006; E05B 81/20

(Continued)

(56) References Cited

U.S. PATENT DOCUMENTS 4,567,894 A * 2/1986 Bergman ............. A61B 5/0555
403/325
4,727,328 A * 2/1988 Carper ................. A61B 6/0442
324/318

(Continued)

FOREIGN PATENT DOCUMENTS

CN   1140403 A   1/1997
CN   1717198 A   1/2006

(Continued)

OTHER PUBLICATIONS

Korean Notice of Allowance for related Korean Application No. 10-2015-0041532, dated Oct. 17, 2016, with English Translation.

(Continued)

*Primary Examiner* — Robert G Santos
*Assistant Examiner* — Myles A Throop
(74) *Attorney, Agent, or Firm* — Lempia Summerfield Katz LLC

(57) ABSTRACT

A medical examination facility is provided, wherein the facility includes an imaging apparatus and a mobile patient table. Mechanical coupling devices to be connected to each other are provided on both the imaging apparatus and the mobile patient table for the purpose of mechanically coupling the patient table to the imaging apparatus in an end position. The mechanical coupling device of the imaging apparatus includes a pulling device that is movable to a locking position via a controllable drive motor. In order to automatically move the patient table, the pulling device engages a driver provided on the patient table, before the end position is reached, and carries it by moving to the locking position, in which the patient table is in the end position.

14 Claims, 3 Drawing Sheets

(58) Field of Classification Search
USPC .................. 5/601; 292/341.12, 341.13, 292/341.15–341.17
See application file for complete search history.

(56) References Cited

U.S. PATENT DOCUMENTS

| | | | |
|---|---|---|---|
| 5,499,415 A | | 3/1996 | McKenna |
| 5,611,638 A * | | 3/1997 | Dorr ............... A61G 7/1019 403/321 |
| 6,499,159 B1 * | | 12/2002 | Schmitt ............... A61B 6/04 192/84.9 |
| 7,293,308 B2 | | 11/2007 | Everett et al. |
| 7,526,823 B2 * | | 5/2009 | Koch ............... A61G 7/1019 5/600 |
| 7,748,511 B1 * | | 7/2010 | Maher ............... G07F 7/0663 194/205 |
| 7,818,839 B2 * | | 10/2010 | Koch ............... A61G 13/08 5/610 |
| 8,061,499 B2 * | | 11/2011 | Khairallah ............... B62H 3/02 194/211 |
| 8,132,276 B2 | | 3/2012 | Klemm et al. |
| 8,533,877 B2 * | | 9/2013 | Weiler ............... A61B 5/0555 5/601 |
| 8,898,837 B2 | | 12/2014 | Iizuka |
| 9,078,628 B2 | | 7/2015 | Cumpson et al. |
| 2006/0167356 A1 * | | 7/2006 | Everett ............... A61B 6/0457 600/407 |
| 2007/0016003 A1 * | | 1/2007 | Piron ............... A61B 5/415 600/415 |
| 2014/0208510 A1 | | 7/2014 | Iizuka |
| 2014/0296692 A1 * | | 10/2014 | Iizuka ............... A61B 5/0555 600/407 |

FOREIGN PATENT DOCUMENTS

| | | |
|---|---|---|
| CN | 101179989 A | 5/2008 |
| CN | 102028495 A | 6/2008 |
| CN | 102125433 A | 7/2011 |
| DE | 102009042873 B3 | 6/2011 |
| DE | 102010005015 A1 | 7/2011 |
| JP | H11197197 A | 7/1999 |
| WO | WO2013042589 A1 | 3/2013 |
| WO | WO2013073550 A1 | 5/2013 |

OTHER PUBLICATIONS

European Search Report for related European Application No. 15151431.2, dated Jun. 11, 2015, with English Translation.
German Office Action for German Application No. 10 2014 205 537.7, dated Jan. 7, 2015, with English Translation.
Chinese Office Action for related Chinese Application No. 2015 1011 3036.5 dated Apr. 1, 2017, with English Translation.

* cited by examiner

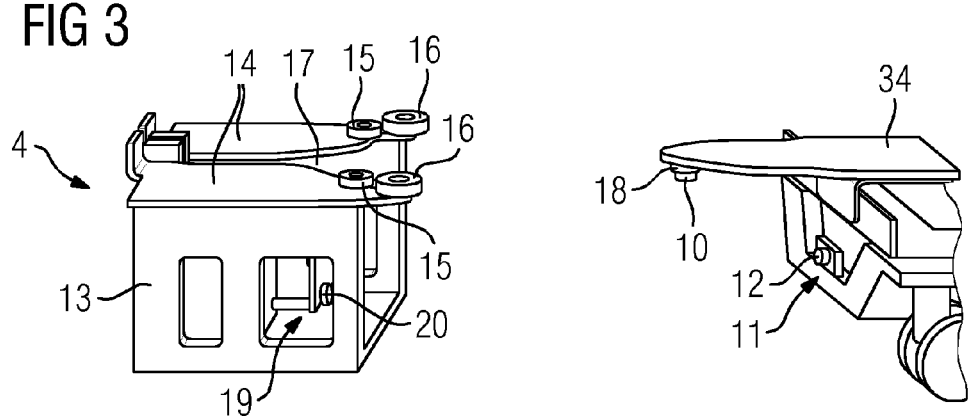
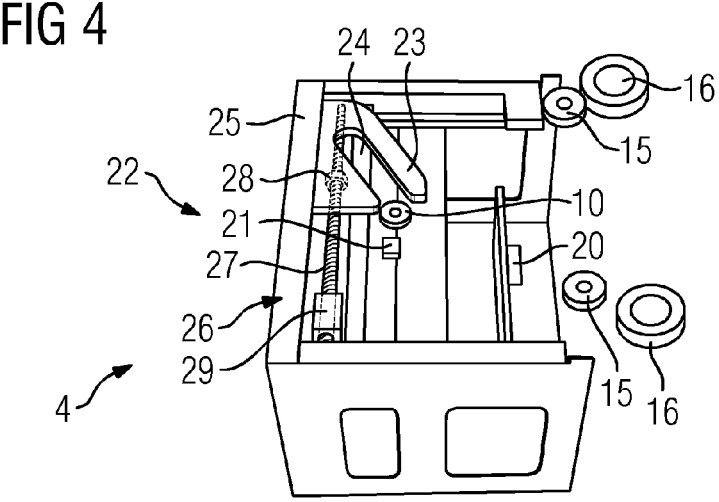
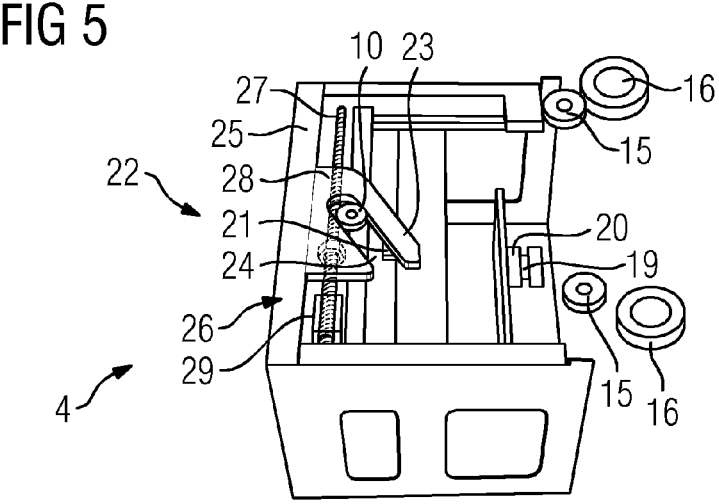

MEDICAL EXAMINATION FACILITY

CROSS-REFERENCE TO RELATED APPLICATIONS

This application claims the benefit of DE 10 2014 205 537.7, filed on Mar. 25, 2014, and DE 10 2014 211 269.9, filed Jun. 12, 2014, which are hereby incorporated by reference in their entireties.

TECHNICAL FIELD

The embodiments relate to a medical examination facility including an imaging apparatus, (e.g., a magnetic resonance scanner), and a mobile patient table, wherein mechanical coupling devices configured to be connected to each other are provided on both the imaging apparatus and the patient table for the purpose of mechanically coupling the patient table to the imaging apparatus in an end position.

BACKGROUND

To perform a magnetic resonance scan, the patient may be conveyed on a mobile patient table to the magnetic resonance scanner. This patient table may include a horizontally movable patient support, with which the patient, when the patient table is positioned at the magnetic resonance scanner, is driven into the tunnel. In order to permit an exact positioning of the patient, the mobile patient table is coupled mechanically to the magnetic resonance scanner, such that both adopt a fixed position relative to each other. For this purpose, corresponding mechanical coupling devices are provided on the magnetic resonance scanner and on the patient table, which coupling devices cooperate with each other and fix the patient table in an end position. An exact and precise reversible positioning of the patient table is provided in order to allow the treatment and imaging operations to take place safely and without interference.

In certain examination facilities, the table-side coupling device takes the form of one or more conical pegs that engage in corresponding mating sockets forming the scanner-side coupling devices and, when the table is pushed farther onto the magnetic resonance scanner, find the correct docking position. The movement of the patient table to the docking station on the magnetic resonance scanner is effected by manual pushing by the operating personnel. The end diameters of the one or more pegs and of the one or more mating sockets are almost the same size, such that in this way the end position is inevitably found. In the end position, the pegs are locked in the sockets, which is effected by corresponding locking hooks that are actuated via a hydraulic system by the operating personnel pressing a foot pedal.

Although reliable mechanical fixing may be achieved in this way, the coupling is rather complicated, particularly on account of the required interaction of the operating personnel.

SUMMARY AND DESCRIPTION

The scope of the present invention is defined solely by the appended claims and is not affected to any degree by the statements within this summary. The present embodiments may obviate one or more of the drawbacks or limitations in the related art.

The object of the embodiments is to provide an improved medical examination facility that permits easier docking of patient tables to imaging apparatus.

To achieve this object in an examination facility of the type mentioned at the outset, a mechanical coupling device of the imaging apparatus is provided. The mechanical coupling device of the imaging apparatus includes a pulling device, which is movable to a locking position via a controllable drive motor and which, in order to automatically move the patient table, engages a driver provided on the patient table, before the end position is reached, and carries it by moving to the locking position, in which the patient table is in the end position.

In an alternative way of achieving this object in an examination facility of the type mentioned at the outset, a mechanical coupling device of the patient table is provided. The mechanical coupling device of the patient table includes a pulling device, which is movable to a locking position via a controllable drive motor and which, in order to automatically move the patient table, engages a driver provided on the imaging apparatus, before the end position is reached, and carries it by moving to the locking position, in which the patient table is in the end position.

A controllable drive motor, and a pulling device that is movable by the drive motor, are provided on the scanner side. This pulling device is movable between a release position and a locking position via the drive motor. When the patient table is pushed forward, the drive motor is correspondingly started up when the table reaches a suitable position, such that the pulling device is moved from the release position. During this movement, the pulling device engages the table-side driver. With continued movement of the pulling device in the direction of the locking position, the driver is forcibly carried along with the pulling device and, consequently, the patient table is forcibly moved in the direction of the magnetic resonance scanner. When the locking position is reached, the patient table is located automatically in the end position, in which the patient table is positioned exactly and in a defined manner relative to the magnetic resonance scanner.

The coupling system of the examination facility has a much simpler construction, and a hydraulic actuation device that requires some interaction on the part of the operating personnel is not provided. Moreover, the motorized locking provides that the patient table itself is moved to the defined end position, such that, in the context of the docking procedure, the patient table is merely brought by the operating personnel to a basic position relative to the imaging apparatus, in which position the pulling device engages the driver. From there on, the entire coupling procedure takes place automatically.

After the scan has been performed, the decoupling takes place in a correspondingly simple way. It is merely necessary to start up the drive motor again, such that the drive motor moves the pulling device in the opposite direction. This leads to the patient table being pushed out from the locking position with positive guidance. When the pulling device reaches the release position, the patient table is freed again, once the driver is no longer engaged. No interaction on the part of the operating personnel is therefore needed for the actual release, since an automatic movement of the patient table takes place from the coupled end position to a release position.

According to a first embodiment, the pulling device may have a linearly movable slotted guide component with a drive slot receiving the driver. The drive slot serves as positive guidance for the driver that, during the linear movement initiated via drive motor, engages in the slot and is guided therein.

As an alternative to the use of a linearly movable slotted guide component, it is also possible to provide a slotted guide component that is rotatable about a rotation axis, with a drive slot receiving the driver. In this embodiment, a rotation movement of the slotted guide component takes place instead of a linear movement. With rotation out from the release position, the driver is positively guided into the drive slot in which, as the rotation movement continues, the driver is carried with positive guidance as far as the locking position.

If a linearly movable slotted guide component is provided, the driver is expediently guided movably on a linear guide, wherein the pulling device includes a spindle drive with a threaded spindle and a nut guided on the latter, to which the slotted guide component is coupled to the nut. The threaded spindle may be driven via the drive motor. The slotted guide component is guided in an exact and sufficiently stable manner via the linear guide. By way of the spindle drive, whose threaded spindle is driven via the drive motor, the slotted guide component may be moved between the release position and the locking position. The slotted guide component on the linear guide may be guided along a linear axis extending perpendicular to the direction of movement of the patient table. That is to say, the slotted guide component moves perpendicularly with respect to the patient table. The drive slot extends at an angle with respect to the linear axis, which angle may be between 30° and 60°. The angled course of the drive slot provides the positive guidance of the driver, and therefore the pulling of the table to the imaging apparatus, when the slotted guide component is moved perpendicularly with respect to the axis of the patient table. Depending on the given angle, an identical linear movement length gives a greater or lesser linear movement path of the patient table, as seen from the position of engagement of the driver in the slot to the attainment of the end position.

According to an embodiment, the rotatable slotted guide component that may be alternatively used is arranged on a rotatably mounted axle bolt, wherein the drive motor drives the axle bolt. The slotted guide component, (e.g., a disk), is rotated by the drive motor between the release position and the locking position, for which purpose it is rotated through 180°, for example. In this embodiment, the drive slot extends in a curve toward the disk interior, such that a linear pulling movement positively takes place.

According to a particularly advantageous embodiment, at least one sensor is provided, via which the position of the patient table, (e.g., the position of the driver), may be detected, wherein the drive motor is controllable according to the detection result of the sensor. When the patient table is pushed in the direction of the imaging apparatus by the operating personnel, the patient table approaches the docking station on the imaging apparatus, and the coupling device provided there. This approach movement is monitored by a sensor. If the sensor, which senses the position of the driver, (e.g., now detects that the driver is located in a correspondingly defined basic position), a corresponding signal is output to a control device. Having been triggered, the control device starts the drive motor, such that the latter correspondingly moves the slotted guide component. The sensor thus detects when the driver is located in the engagement position, in which driver may engage in the slot. As soon as the slotted guide component is moved, the driver is guided into the slot, whereupon the automatic pulling movement begins. The pulling-in is thus started automatically.

A guide component supporting the driver may be provided on the patient table and, on approaching the magnetic resonance scanner, engages between two guide rollers arranged on the coupling device there and is guided by the guide rollers until the end position is reached. This guide component therefore provides guiding on both sides. In other words, the patient table is laterally guided during the automatic pulling-in movement. These guide rollers may be provided in pairs on both sides of the pulling-in channel or the pulling-in plane, such that the guide component is therefore supported and guided twice on each side. The guide component may be a conical guide plate that may be provided with a radius contour at the edge.

In order to provide an electrical coupling of the patient table to the imaging apparatus by the automatic pulling-in, as is needed to allow a central control device of the imaging apparatus to control the movement path of the couch panel that is movable automatically via a corresponding drive motor, electrical coupling devices are provided at the imaging apparatus and the patient table. The electrical coupling devices are provided for the purpose of electrically coupling the patient table to the imaging apparatus in the end position, which coupling devices are automatically connected to each other at the latest when the end position is reached. The electrical coupling devices are in this case configured, for example, as a plug/socket pairing. Therefore, when the patient table has been automatically pulled into the end position, the plug and the socket are also automatically brought together, providing electrical contact. This is readily possible in view of the fact that the pulling-in movement is a linear movement and leads to a defined end position. In other words, the plug is guided exactly into the socket without the need for any interaction on the part of the operating personnel. The electrical coupling devices may be assigned centering devices, which interact with each other when moved together. For example, the table-side plug may be provided with a cone-like outer contour that surrounds the plug and is driven into a corresponding cone-like inner contour surrounding the scanner-side socket, or similar.

The patient table is sometimes provided with its own drive motor, which drives at least two table-side rollers, such that the table is self-propelled. With this dedicated drive, the table is able to travel to a position close to the imaging apparatus. In order to allow a table of this configuration to be pulled in automatically without blocking a table-side roller after it has been coupled to the drive motor as described, it is expedient if a sensor is provided on the table. The sensor detects when the patient table approaches the imaging apparatus, wherein the rollers are switched to idle according to the sensor detection. This provides either that the rollers are decoupled from the drive motor or that the drive motor is switched to idle, such that the rollers may turn freely and the pulling device may pull the table to the end position after engaging the driver.

BRIEF DESCRIPTION OF THE DRAWINGS

FIG. 3 depicts an enlarged partial view of an embodiment of the patient table and of the docking station with the mechanical coupling devices.

FIG. 4 depicts a partial view of an embodiment of the docking station of the magnetic resonance scanner, together with the table-side driver in a starting position before the mechanical coupling begins, FIG. 5 depicts the view from FIG. 4 after the mechanical coupling.

DETAILED DESCRIPTION

The embodiments are described below using the example of a magnetic resonance scanner. Embodiments with other imaging apparatus, (e.g., computed tomography scanners for X-ray imaging), are constructed analogously.

Figure 1:
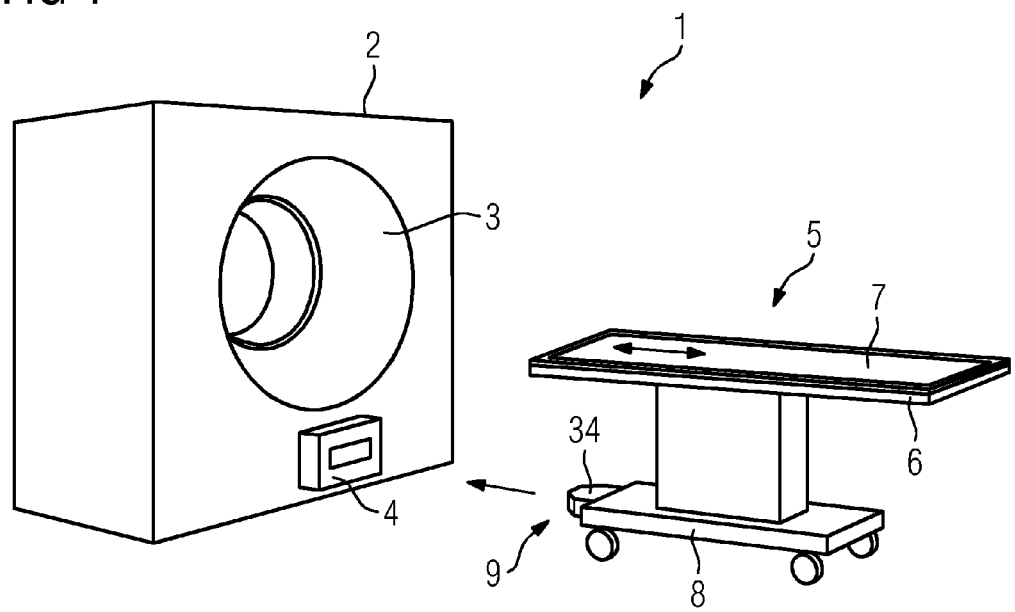
FIG. 1 depicts a diagrammatic representation of an embodiment of a medical examination facility.

FIG. 1 depicts a medical examination facility 1 in a purely diagrammatic representation, including a magnetic resonance scanner 2 with a tunnel 3, and with a docking station 4 provided on the front. The docking station 4 includes mechanical coupling devices assigned to the scanner, as will be discussed in more detail below.

The examination facility 1 further includes a patient table 5. The patient table 5 includes a couch 6 with a couch panel 7 that is movable horizontally in the longitudinal direction of the table. On a chassis 8, a mechanical coupling device 9 is provided that cooperates with the docking station 4 in order to bring the patient table 5 to a defined position relative to the magnetic resonance scanner 2. During operation, the patient table 5 is moved in the direction of the magnetic resonance scanner 2 either manually by the operating personnel or, in automatic drive mode, in a suitably controlled manner, such that the docking station 4 and the coupling device 9 are driven one into the other, whereupon an automatic locking procedure starts, which is explained in more detail below.

Figure 2:
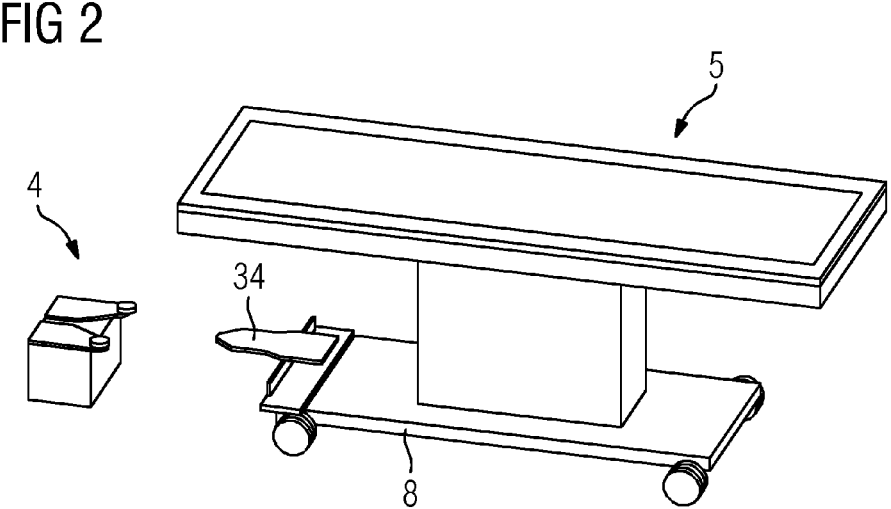
FIG. 2 depicts a partial view of an embodiment of the patient table and of the scanner-side docking station.

FIG. 2 depicts a detailed view of the patient table 5 and, as part of the magnetic resonance scanner, the docking station 4 of the latter. A guide plate 34, arranged on the chassis 8 of the patient table 5, has a conical basic shape and is provided at the edges with a radius contour. On its underside, a driver 10 is provided, which represents a central coupling component of the patient table 5. Furthermore, an electrical coupling device 11 is provided on the chassis and includes a plug 12, which cooperates with a corresponding coupling device on the docking station 4, as is likewise explained in more detail below. An example of this plug 12 is depicted in FIG. 3.

The docking station 4 has a corresponding housing 13, on the top of which two centering plates 14 are provided, with two pairs of rollers 15, 16 arranged at the front end of each of the centering plates 14. A tapering guide slit 17 remains between the two centering plates 14. When patient table 5 and docking station 4 are brought together, the guide plate 34 is moved between the pairs of centering rollers 15, 16 and is guided by the centering rollers 15, 16. At the same time, the driver 10, or an upper collar 18 of widened diameter, engages in the guide slit 17 and is guided therein. The patient table 5 is moved until the table 5 is in a basic position, starting from which the automatic mechanical coupling procedure may take place. As may be seen from FIG. 3, a scanner-side electrical coupling device 19 is provided in the interior of the housing 13 and is designed as a socket 20 into which the plug 12 is automatically pulled during the mechanical coupling, such that an electrical coupling is also obtained at the same time.

Omitting the centering plates 14 in particular, but depicting the corresponding centering rollers 15, 16, FIG. 4 depicts a diagrammatic representation of the docking station 4 and, as part of the patient table 5, the driver 10. For reasons of clarity, all the other parts of the table are not depicted. As has been described, the conical guide plate 34 is guided laterally between the pairs of centering rollers 15, 16, and the collar 18 is guided in the guide slit 17. This guiding takes place until a basic position depicted in FIG. 4 is reached, which position is detected by a sensor 21 integrated on the docking station 4. In this basic position, the driver 10 is located in a defined position relative to the mechanical coupling device 22 of the scanner or of the docking station 4. This mechanical coupling device 22 includes a slotted guide component 23 with a drive slot 24, which slotted guide component 23 is movable on a linear guide 25 in a direction perpendicular to the movement axis of the patient table. For this purpose, a spindle drive 26 including a spindle 27 and a nut 28 running on the spindle 27, here indicated only by broken lines, is provided. The slotted guide component that, as has been described, is guided in the linear guide 25, is secured on this nut 28. The threaded spindle 27 is rotatable via a drive motor 29, such that the nut 28 may be moved linearly together with the slotted guide component 23.

In the basic position depicted in FIG. 4, the driver 10 is located more or less at the entrance of the drive slot 24, which extends at an angle of ca. 45° relative to the axis of the linear guide 25. With the detection signal output via the sensor 21, the drive motor 29 is started up via a control device of the magnetic resonance scanner, such that the threaded spindle 27 rotates and the nut 28 is moved together with the slotted guide component 23 along the linear guide 25. As a result of this movement, the driver 10 runs into the drive slot 24 and, within the latter, in a direction perpendicular to the axis of the linear guide 25. The end position is depicted in FIG. 5. As may be seen, the driver 10 is located at the bottom or end of the drive slot 24 and, proceeding from the basic position according to FIG. 4, is now in a pulled-in end position near the linear guide 25. That is to say, it has been pulled actively into an end position by the purely linear movement of the slotted guide component 23 automated via the drive motor 29. The patient table 5 is firmly locked mechanically in this end position, on the one hand since the driver 10 is in a fixed position, and, on the other hand, since the guide plate 34 is secured laterally between the pairs of centering rollers 15, 16 and via the collar 18 in the guide slit 17. The slotted guide component thus constitutes a pulling device that is movable via the drive motor 29 and spindle drive 26 and via which the patient table is pulled automatically into a defined end position.

At the same time as the automatic pulling in, the plug 19 is also coupled to the socket 20, such that the patient table is also coupled electrically to the docking station, and the operation of the patient table 5, or the automated movement of the couch panel 7, may be controlled via the control device of the magnetic resonance scanner 2.

The renewed release of the coupling takes place in a similarly simple and automated manner like the pulling-in movement. For this purpose, the drive motor 29 is operated in the opposite direction when a corresponding control signal is output, such that the threaded spindle 27 likewise rotates in the opposite direction. Additionally, proceeding from the end position depicted in FIG. 5, the nut 28 migrates back again to the basic position depicted in FIG. 4. The driver 10 runs out of the drive slot 24 in this process, after which the driver 10, and with it the patient table 5, is pushed out automatically in the opposite direction. When the basic position according to FIG. 4 is reached, the patient table 5 may be driven back manually, or by its own drive, away from the scanner 2. At the same time, this of course also provides an automatic decoupling of the electrical coupling.

Figure 6:
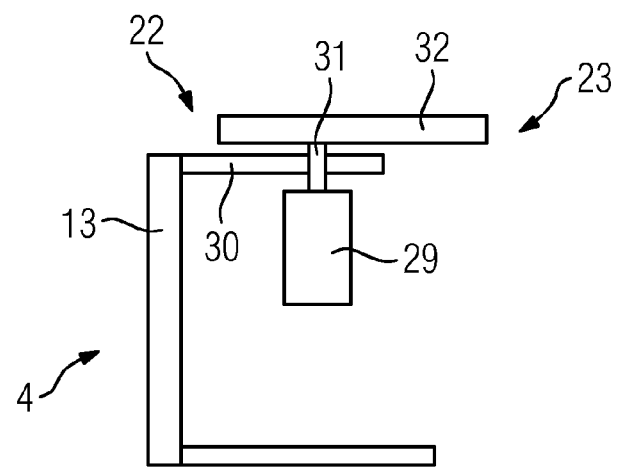
FIG. 6 depicts a diagrammatic representation of part of a docking station in a second embodiment, in a side view.
Figure 7:
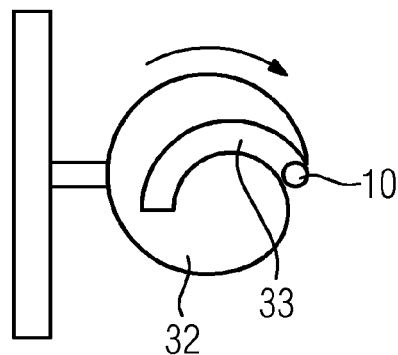
FIG. 7 depicts the view from FIG. 6 from the top, with the table-side driver depicted in a basic position before the coupling procedure begins.
Figure 8:
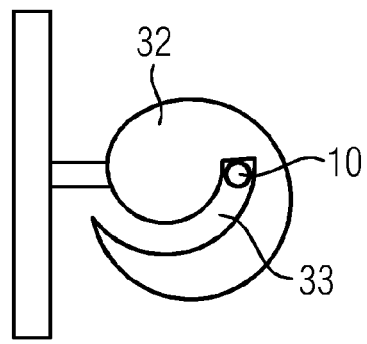
FIG. 8 depicts the view according to FIG. 7 at the end of the coupling procedure.

FIGS. 6-8 depict, in a diagrammatic representation, a further embodiment of a docking station 4 with its mechanical coupling device 22, with the same reference signs being used as far as possible for the same components. On the housing 13, depicted only symbolically here, a slotted guide component 23 in the form of a disk 32 is mounted rotataby in a fixed position on a suitable support 30 via an axle bolt 31. The drive motor 29 adjoins the axle bolt 31, that is to say the axle bolt 31, and with it the disk 32, may be rotated via the drive motor 29.

FIG. 7 depicts, in a diagrammatic representation, the basic position, comparable to the view according to FIG. 4. The driver 10 has again been detected by a sensor, thereby providing that the driver is located in the basic position. After this, the drive motor 29 is started up via the control device on the scanner side, such that the disk 32 is rotated. The disk 32 in turn has a drive slot 33 that, however, in this case winds inward from the outside. In the basic position, the driver 10 is located at the entrance to the drive slot 33. If the disk now rotates, the driver 10 is pulled into the drive slot 33 and, as a result of the rotation of the disk, migrates within the latter to the slot end that is located much farther inward in relation to the edge of the disk. In the end position, the driver 10 has been pulled fully into the drive slot 33 (see FIG. 8). The driver thus also moves here linearly toward the magnetic resonance scanner 2, which leads to a corresponding pulling-in of the patient table 5. The disk 32 here is also a pulling device that is movable via the drive motor 29 and automatically pulls the patient table into a defined end position.

The corresponding lateral guides via the centering plates 14 with the pairs of centering rollers 15, 16 on the docking station 4, and the corresponding guide plate 34 with its conical and curved side shape, are of course also provided, such that a corresponding lateral guide is also obtained. An exact mechanical coupling, achieved automatically by the pulling-in, is once again provided. At the same time, the corresponding electrical coupling is also achieved, since the plug on the table side and socket on the scanner side are also provided in this configuration.

To release the coupling again, the disk 32 is rotated in the opposite direction via the drive motor 29. This leads to a corresponding positive guidance of the driver 10 in the drive slot 33, in which it runs to the slot exit and is thus necessarily pushed away from the scanner, as of course also is the patient table 5.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description. In particular, a reverse arrangement is also possible in which the controllable drive motor 29 is arranged in the patient table 5 and the driver 10 is arranged on an imaging apparatus.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A medical examination facility comprising:
   an imaging apparatus comprising a first mechanical coupling device; and
   a mobile patient table comprising a second mechanical coupling device,
   wherein the first and second mechanical coupling devices are configured to be connected to each other for the purpose of mechanically coupling the patient table to the imaging apparatus in an end position,
   wherein one of the first mechanical coupling device of the imaging apparatus or the second mechanical coupling device of the patient table comprises a pulling device that is movable to a locking position via a controllable drive motor, the pulling device comprising a linearly movable slotted guide component with a drive slot configured to receive a driver, a spindle drive with a threaded spindle, and a nut guided on the threaded spindle, wherein the nut is coupled with the linearly moveable slotted guide component and the threaded spindle is configured to be driven via the drive motor,
   wherein the other of the first mechanical coupling device of the imaging apparatus or the second mechanical coupling device of the patient table comprises the driver,
   wherein the pulling device is configured to automatically move the patient table by engaging the driver, opposite the pulling device, via the linearly moveable slotted guide component before the end position is reached, and carrying the patient table by moving to the locking position, in which the patient table is in the end position, and
   wherein the linearly moveable slotted guide component is guided along a linear axis extending perpendicular to a direction of movement of the patient table.

2. The medical examination facility as claimed in claim 1, wherein the driver is provided on the patient table, and wherein the first mechanical coupling device of the imaging apparatus comprises the pulling device.

3. The medical examination facility as claimed in claim 1, wherein the driver is provided on the imaging apparatus, and wherein the second mechanical coupling device of the patient table comprises the pulling device.

4. The medical examination facility as claimed in claim 1, wherein at least one sensor is provided to detect a position of the patient table, wherein the drive motor is controllable according to a detection result of the sensor.

5. The medical examination facility as claimed in claim 1, wherein at least one sensor is provided to detect a position of the driver of the patient table, wherein the drive motor is controllable according to a detection result of the sensor.

6. The medical examination facility as claimed in claim 1, wherein a guide component is provided on the patient table or on the imaging apparatus, wherein the guide component, on approaching the pulling device, engages between two guide rollers arranged on the first or second coupling device and is guided by the guide rollers until the end position is reached.

7. The medical examination facility as claimed in claim 6, wherein two pairs of guide rollers lying opposite each other are provided.

8. The medical examination facility as claimed in claim 6, wherein the guide component is a guide plate having a conical profile.

9. The medical examination facility as claimed in claim 8, wherein the guide plate has a radius contour at an edge of the guide plate.

10. The medical examination facility as claimed in claim 1, wherein electrical coupling devices are furthermore provided on the imaging apparatus and on the patient table for the purpose of electrically coupling the patient table to the imaging apparatus in the end position, wherein the electrical coupling devices are automatically connected to each other at least when the end position is reached.

11. The medical examination facility as claimed in claim 10, wherein the electrical coupling devices are configured as a plug/socket pairing.

12. The medical examination facility as claimed in claim 11, wherein the electrical coupling devices are assigned centering devices that cooperate with each other when brought together.

13. The medical examination facility as claimed in claim 12, wherein the centering devices comprise:
    a first centering device having two centering plates and at least one centering roller positioned on an end of each centering plate; and
    a second centering device having a guide plate configured to move between the centering plates guided by the centering rollers.

14. The medical examination facility as claimed in claim 1, wherein the patient table comprises at least two rollers drivable via a table-side drive motor, and in that a sensor is provided that detects when the patient table approaches the imaging apparatus, wherein the rollers are switched to idle according to a sensor detection.

* * * * *